US011980771B2

(12) United States Patent
Holmes

(10) Patent No.: US 11,980,771 B2
(45) Date of Patent: May 14, 2024

(54) PROCESSING OPTICAL COHERENCE TOMOGRAPHY (OCT) SCANS

(71) Applicant: MICHELSON DIAGNOSTICS LIMITED, Kent (GB)

(72) Inventor: Jonathan Denis Holmes, Kent (GB)

(73) Assignee: MICHELSON DIAGNOSTICS LTD, Kent (GB)

( * ) Notice: Subject to any disclaimer, the term of this patent is extended or adjusted under 35 U.S.C. 154(b) by 436 days.

(21) Appl. No.: 16/484,712

(22) PCT Filed: Jan. 29, 2018

(86) PCT No.: PCT/GB2018/050243
§ 371 (c)(1),
(2) Date: Aug. 8, 2019

(87) PCT Pub. No.: WO2018/146452
PCT Pub. Date: Aug. 16, 2018

(65) Prior Publication Data
US 2020/0038678 A1 Feb. 6, 2020

(30) Foreign Application Priority Data
Feb. 8, 2017 (GB) .................................. 1702098

(51) Int. Cl.
A61N 5/06 (2006.01)
A61B 5/00 (2006.01)
(Continued)

(52) U.S. Cl.
CPC .......... A61N 5/0616 (2013.01); A61B 5/0066 (2013.01); A61B 5/1032 (2013.01);
(Continued)

(58) Field of Classification Search
CPC ................. A61N 5/0616; A61N 5/067; A61N 2005/0626; A61N 2005/0627;
(Continued)

(56) References Cited

U.S. PATENT DOCUMENTS 7,540,869 B2 * 6/2009 Altshuler ............. A61B 18/203
606/9
2003/0036751 A1 2/2003 Anderson et al.
(Continued)

FOREIGN PATENT DOCUMENTS

| GB | 2496895 A | 5/2013 |
| GB | 2540390 A | 1/2017 |

(Continued)

OTHER PUBLICATIONS

"Gambichler et al., "Recent advances in clinical application of optical coherence tomography of human skin", Jul. 7, 2015, Dove Press Journal: Clinical, Cosmetic and Investigational Dermatology." (Year: 2015).*
(Continued)

Primary Examiner — Carl H Layno
Assistant Examiner — Aya Ziad Bakkar
(74) Attorney, Agent, or Firm — Burns & Levinson LLP; Steven M. Mills

(57) ABSTRACT

A method of and apparatus for processing optical coherence tomography (OCT) scans through a subject's skin, the method comprising, using a computing device (1): receiving a plurality of OCT scans through the subject's skin (7), the OCT scans representing an OCT signal in slices through the subject's tissue; processing the OCT scans to determine a set of parameters; processing each parameter to determine a set of control settings for an energy-delivery device (20); transmitting the control settings from the computing device (1) to the energy-delivery device (20); in which the set of param-
(Continued)

eters comprises the depth of the superficial plexus (108) through the subject's skin (7).

21 Claims, 9 Drawing Sheets

(51) Int. Cl.
*A61B 5/103* (2006.01)
*A61B 5/107* (2006.01)
*A61B 18/00* (2006.01)
*A61B 18/20* (2006.01)
*A61N 5/067* (2006.01)

(52) U.S. Cl.
CPC .......... *A61B 5/1075* (2013.01); *A61B 5/1079* (2013.01); *A61B 5/442* (2013.01); *A61B 5/448* (2013.01); *A61B 5/489* (2013.01); *A61B 18/203* (2013.01); *A61B 2018/0047* (2013.01); *A61B 2018/00577* (2013.01); *A61B 2018/00642* (2013.01); *A61B 2018/00732* (2013.01); *A61N 2005/0626* (2013.01); *A61N 2005/0627* (2013.01); *A61N 5/067* (2021.08)

(58) Field of Classification Search
CPC ... A61B 5/0066; A61B 5/1032; A61B 5/1075; A61B 5/1079; A61B 5/442; A61B 5/448; A61B 5/489; A61B 18/203; A61B 2018/0047; A61B 2018/00577; A61B 2018/00642; A61B 2018/00732
See application file for complete search history.

(56) References Cited

U.S. PATENT DOCUMENTS

2007/0213696 A1  9/2007  Altshuler et al.
2016/0317226 A1* 11/2016  Jagdeo ................... A61B 90/06
2016/0371836 A1* 12/2016  Kuno ..................... G06T 11/008

FOREIGN PATENT DOCUMENTS

| WO | 2008/072151 A2 | 6/2008 |
| WO | 2014/207003 A1 | 12/2014 |
| WO | 2015/070106 A1 | 5/2015 |
| WO | 2015/071099 A1 | 5/2015 |

OTHER PUBLICATIONS

International Search Report and Written Opinion from related PCT Application No. PCT/GB2018/050243, dated May 7, 2018 (15 pages).

Search Report from related United Kingdom Application No. GB1702098.3, dated Sep. 27, 2017 (7 pages).

* cited by examiner

PROCESSING OPTICAL COHERENCE TOMOGRAPHY (OCT) SCANS

CROSS REFERENCE TO RELATED APPLICATIONS

This application is the U.S. national phase entry under 35 U.S.C. § 371 of International Application No. PCT/GB2018/050243, filed Jan. 29, 2018, entitled "PROCESSING OPTICAL COHERENCE TOMOGRAPHY (OCT) SCANS", which claims priority to United Kingdom Patent Application No. 1702098.3, filed Feb. 8, 2017, the contents of which are incorporated herein by reference in their entirety for all purposes.

BACKGROUND

This invention relates to a method of and apparatus for processing optical coherence tomography scans, and a skin energy-delivery apparatus.

In the field of medical and aesthetic dermatology, energy-delivery devices such as lasers, Light Emitting Diodes (LED), Ultraviolet Light Sources, and Radio-Frequency (RF) emitters, are used for treating tissue, especially skin but also other tissues of the human body.

Some Examples are:
$CO_2$ and Er:YAG lasers used for ablative, non-ablative and fractional resurfacing of the skin for the purposes of skin rejuvenation, scar treatment, pigmented spot removal, wrinkle removal;
Intense Pulse Light (IPL) sources, which are based on high intensity LEDs, used for similar applications to the above and for treating vascular lesions;
Pulse Dye Lasers (PDL) and Nd:YAG lasers used for treating Port Wine Stains, Rosacea, Hemangiomas, Spider veins and other vascular lesions, and also pigmented spots;
PDL and Nd:YAG lasers for hair removal;
RF sources for 'skin tightening' and skin rejuvenation;
Ultraviolet sources for treating Psoriasis plaques;
Pico-second pulsed lasers for tattoo removal
This list is not complete and there are many other examples. Other tissue apart from skin is also treated with these devices, such as female genitals and oral mucosa.

However, in all cases, the dose of energy delivered by the device is pre-set by the user based on a combination of visual assessment of the patient's condition, previous experience gained by the user in treating similar patient conditions in the past, and on 'preferred settings' derived from published literature and the manufacturers' manuals. This is less than ideal, because the treatment settings therefore do not take into account the specific subsurface condition of the individual patient's skin or other tissue. They may also not take into account the variability naturally present between different locations on the patient's body or face, for example between the skin on the nose, cheek, eyelid, chin, neck etc. Because this underlying variability of the tissue to be treated is not known, the efficacy of the treatment, and the safety of the treatment, may be compromised. If the energy dose is too large or delivered too quickly, permanent scarring may result, which is highly undesirable. If the energy dose is too small, or delivered too slowly, the treatment may have little effect on the lesion, with unsatisfactory results for the patient. A corollary of the risk of scarring is that users tend to err on the side of caution, often resulting in smaller ineffective doses. This may in turn result in many more treatment sessions for the patient to achieve the desired result, which is expensive and undesirable. Only highly experienced users can get the best results from these devices.

One of these laser treatments is 'skin rejuvenation' which is achieved by using the laser (or intense pulse light source) to deliver energy into skin causing it to be damaged such that a healing response is created, and when healed the resulting skin has less wrinkles and has a more youthful appearance than the untreated skin. There are a number of different treatments of this type, for example (but not limited to):
Full-field ablative laser, which completely removes the top layers of the skin
Fractional ablative laser, which removes skin in a matrix of holes
Non-ablative laser (both full-field and fractional), which does not remove the tissue but nevertheless causes it to partially cauterise or 'coagulate'
Intense Pulse Light, which is similar to non-ablative laser but uses a high intensity light source instead
In summary, there is a need for a means of making rapid, repeatable, accurate non-invasive assessment of skin or other tissue, such that the energy delivery by an energy-delivery device can be optimised to suit the specific condition of the tissue to be treated, maximising efficacy and consistency without compromising safety.

Currently, dermatologists assess skin health visually and by touch. Those skilled in the art will be aware that there exist on the market a variety of instruments which are used to measure properties of the skin. This include, but are not limited to: skin roughness/profile measurement devices (PRIMOSlite, Canfield Scientific, Parsippany, USA), transepidermal water loss measurement devices (Tewameter TM300, Courage & Khazaka, Cologne, Germany), skin flexibility measurement devices (Cutometer dual MPA 580, Courage & Khazaka, Cologne, Germany), high resolution skin imaging devices (Vivascope 3000, Caliber I.D., Rochester, NY, USA). These devices all measure individual parameters of the skin which can be of value in assessing skin. However, they suffer from a variety of disadvantages; the most important being that with each such device, only one aspect of the skin is measured, but the users ideally requires multiple aspects in order to obtain a fuller picture of the tissue and to define the treatment parameters. In practice, no individual device has become established as a standard tool for assessing skin health.

SUMMARY

In a first aspect of the invention, there is provided a method of processing optical coherence tomography (OCT) scans through a subject's skin, the method comprising, using a computing device:
receiving a plurality of OCT scans through the subject's skin, the OCT scans representing an OCT signal in slices through the subject's tissue;
processing the OCT scans to determine a set of parameters;
processing each parameter to determine a set of control settings for an energy-delivery device;
transmitting the control settings from the computing device to the energy-delivery device;
in which the set of parameters comprises the depth of the superficial plexus through the subject's skin.

As such, we have appreciated that the above method can be used to control an energy-delivery device based upon the position of the superficial plexus. Furthermore, we have appreciated that the position of the superficial plexus is an important parameter, as if the energy is delivered too deeply into the subject's skin causing significant damage to the superficial vascular plexus, scarring can result.

As such, the control settings may comprise a range of depths to which energy is to be delivered; the maximum depth may be less than, or proportional to, the depth of the superficial plexus. Where the maximum depth is proportional to the depth of the superficial plexus, the maximum depth may at most twice, 1.5, 1.2 or 1.1 times the depth of the superficial plexus. As such, whilst the energy may reach the superficial plexus and extend into it, it may not extend sufficiently to fully destroy it.

The determination of the depth of the superficial plexus may comprise determining the position of a surface of the subject's skin in the scans. Thus, the depth can then be related to depth through the skin, rather than simply depth through the scan as such.

The depth of the superficial plexus may be determined by determining a profile of the lengths of blood vessel segments in the scans at varying depth. Typically, the depth of the superficial plexus may be determined as a depth at which there are more than a first threshold of blood vessel segments which are longer than a second threshold.

The set of parameters may comprise the density of vessels in the superficial plexus. Low density of vessels may correspond to poor potential healing, requiring a less aggressive treatment. Typically, the set of control settings will comprise a measure of the energy delivered to the skin. In one example, the density of vessels may comprise the number of vessel segments per unit area in the scans at varying depth. In another example, the density of vessels may comprise the fraction of the scan area comprising vessels at varying depth.

The set of parameters may further comprise blood vessel diameter, particularly of the superficial plexus. We have appreciated that unhealthy skin may have thinner vessels than healthy skin. As such, the method may comprise processing the scans to determine at least one of the mean, median, upper and lower quartile diameter of vessels at varying depth.

The set of parameters may further comprise an indication of the level of skin appendages in the subject's skin. Skin appendages may comprise hairs, follicles and pores. The determination of the level of skin appendages may comprise building an en-face depth scan of the subject's skin, and determining the presence of skin appendages therein. Typically, the en-face scan will be built at a depth through the skin below but adjacent to the dermis-epidermis junction. The level may be the number-density per unit area.

The set of parameters may comprise an optical attenuation of the skin, typically measured as the rate at which the logarithm of the OCT signal falls with depth below the skin surface. This has been found to be higher for skin that has a high collagen density.

The set of parameters may comprise skin roughness. This is a measure of the surface topography of the skin. The determination of the skin roughness may comprise the determination of the mean deviation of the skin position from the mean skin position (known as $R_a$), the range of skin position from the highest peak to lowest valley (known as $R_z$) or the root mean square deviation of the skin position (known as $R_q$). More wrinkled skin has higher roughness and may require more aggressive treatment to achieve an acceptable result.

The set of parameters may comprise epidermal thickness (or mean depth of the dermis-epidermis junction). It is appreciated that a thinner epidermis occurs in skin which is older, less healthy, or in more delicate parts of the anatomy, all of which may reduce skin healing potential or propensity to scar. Typically, the epidermis produces a lower OCT signal than the dermis. The determination of the epidermal thickness may comprise detection of the depth at which there is a sudden increase in mean OCT signal with depth.

The set of parameters may comprise skin colour. As such, the method may comprise capturing an image of the skin. Skin which has a higher melanin content will appear darker, which may result in a different depth of penetration of the energy delivery than light skin with low melanin.

The set of parameters may comprise at least one of the following:
Depth of wrinkles
Skin reflectivity
Depth of epidermis
Density of vessels in the superficial vascular plexus in the upper dermis
Optical attenuation versus depth The energy-delivery device may comprise a laser. In some examples, the energy delivery device could comprise at least one of:
Full-field ablative laser, which typically completely removes the top layers of the skin
Fractional ablative laser, which typically removes skin in a matrix of holes
Non-ablative laser (both full-field and fractional), which typically does not remove the tissue but nevertheless causes it to partially cauterise or 'coagulate'
Intense Pulse Light, which is typically similar to non-ablative laser but uses a high intensity light source instead.

Typically, the control settings will comprise at least one of:
pulse duration
pulse energy
fluence (that is, energy delivered per unit area)
beam depth
beam diameter
number of pulses per treatment The method may comprise allowing an operator to modify the settings before they are used in the energy-delivery device.

Typically, the method will comprise using the control settings in the energy-delivery device to deliver energy to the subject's skin.

The computing device may be remote from the energy-delivery device, and may in some embodiments comprise multiple interacting computing devices (typically, some form of distributed computing). The computing device may, for example, at least in part form part of an OCT scanning device from which the OCT scans are obtained, or again may be remote therefrom. Alternatively the computing device may form part of the energy-delivery device, and as such the method may comprise conveying the OCT scans to the energy-delivery device.

In a second aspect of the invention, there is provided apparatus for processing optical coherence tomography (OCT) scans through a subject's skin, the apparatus comprising a computing device arranged to:
receive a plurality of OCT scans through the subject's skin, the OCT scans representing an OCT signal in slices through the subject's tissue;
process the OCT scans to determine a set of parameters;
process each parameter to determine a set of control settings for an energy-delivery device;
transmit the control settings to the energy-delivery device;
in which the set of parameters comprises the depth of the superficial plexus through the subject's skin.

As such, we have appreciated that the above apparatus can be used to control an energy-delivery device based upon the position of the superficial plexus. Furthermore, we have appreciated that the position of the superficial plexus is an important parameter, as if the energy is delivered too deeply into the subject's skin causing significant damage to the superficial plexus, scarring can result.

As such, the control settings may comprise a range of depths to which energy is to be delivered; the maximum depth may be less than, or proportional to, the depth of the superficial plexus. Where the maximum depth is proportional to the depth of the superficial plexus, the maximum depth may at most twice, 1.5, 1.2 or 1.1 times the depth of the superficial plexus. As such, whilst the energy may reach the superficial plexus and extend into it, it may not extend sufficiently to fully destroy it.

The computing device may be arranged such that the determination of the depth of the superficial plexus comprises determining the position of a surface of the subject's skin in the scans. Thus, the depth can then be related to depth through the skin, rather than simply depth through the scan as such.

The computing device may be arranged such that the depth of the superficial plexus is determined by determining a profile of the lengths of blood vessels in the scans at varying depth. Typically, the depth of the superficial plexus may be determined as a depth at which there are more than a first threshold of blood vessels which are longer than a second threshold.

The set of parameters may comprise the density of vessels in the superficial plexus. Low density of vessels may correspond to poor potential healing, requiring a less aggressive treatment. Typically, the set of control settings will comprise a measure of the energy delivered to the skin. In one example, the density of vessels may comprise the number of vessel segments per unit area in the scans.

The set of parameters may further comprise blood vessel diameter, particularly of the superficial plexus. We have appreciated that unhealthy skin may have thinner vessels than healthy skin. As such, the method may comprise processing the scans to determine at least one of the mean, median, upper and lower quartile diameter of vessels.

The set of parameters may further comprise an indication of the level of skin appendages in the subject's skin. Skin appendages may comprise hairs and follicles. The determination of the level of skin appendages may comprise building an en-face scan of the subject's skin, and determining the presence of skin appendages therein. Typically, the en-face scan will be built at a depth through the skin below but adjacent to the epidermis-dermis junction. The level may be the number-density per unit area.

The set of parameters may comprise an optical attenuation of the skin, typically measured as the rate at which the OCT signal falls with depth below the skin surface. This has been found to be higher for skin that has a high collagen density.

The set of parameters may comprise skin roughness. This is a measure of the surface topography of the skin. The determination of the skin roughness may comprise the determination of the mean deviation of the skin position from the mean skin position (known as $R_a$), the range of skin position from the highest peak to lowest valley (known as $R_z$) or the root mean square deviation of the skin position (known as $R_q$). More wrinkled skin has higher roughness and may require more aggressive treatment to achieve an acceptable result.

The set of parameters may comprise epidermal thickness (or mean depth of the dermis-epidermis junction). It is appreciated that a thinner epidermis occurs in skin which is older, less healthy, or in more delicate parts of the anatomy, all of which may reduce skin healing potential or propensity to scar. Typically, the epidermis produces a lower OCT signal than the dermis. The determination of the epidermal thickness may comprise detection of the depth at which there is a sudden increase in mean OCT signal with depth.

The set of parameters may comprise skin colour. As such, the apparatus may comprise a camera, typically arranged to capture an image of the skin. Skin which has a higher melanin content will appear darker, which may result in a different depth of penetration of the energy delivery than light skin with low melanin.

The set of parameters may comprise at least one of the following:
Depth of wrinkles
Skin reflectivity
Depth of epidermis
Density of vessels in the superficial vascular plexus in the upper dermis
Optical attenuation versus depth The energy-delivery device may comprise a laser. In some examples, the energy delivery device could comprise at least one of:
Full-field ablative laser, which typically completely removes the top layers of the skin
Fractional ablative laser, which typically removes skin in a matrix of holes
Non-ablative laser (both full-field and fractional), which typically does not remove the tissue but nevertheless causes it to partially cauterise or 'coagulate'
Intense Pulse Light, which is typically similar to non-ablative laser but uses a high intensity light source instead.

Typically, the control settings will comprise at least one of:
pulse duration
pulse energy
fluence (that is, energy delivered per unit area)
beam depth
beam diameter
number of pulses per treatment The computing device may be arranged to allow an operator to modify the settings before they are used in the energy-delivery device.

According to a third aspect of the invention, there is provided a skin energy-delivery apparatus comprising the apparatus of the second aspect of the invention and an energy-delivery device arranged to deliver energy to a subject's skin.

Typically, the energy-delivery apparatus will be arranged so as to use the control settings in the energy-delivery device to deliver energy to the subject's skin.

The computing device may be remote from the energy-delivery device, and may in some embodiments comprise multiple interacting computing devices (typically, some form of distributed computing). The computing device may, for example, at least in part form part of an OCT scanning device from which the OCT scans are obtained, or again may be remote therefrom. Alternatively the computing device may form part of the energy-delivery device.

BRIEF DESCRIPTION OF THE DRAWINGS

There now follows, by way of example, description of embodiments of the invention, described with reference to the accompanying drawings, in which.

DETAILED DESCRIPTION

Figure 1:
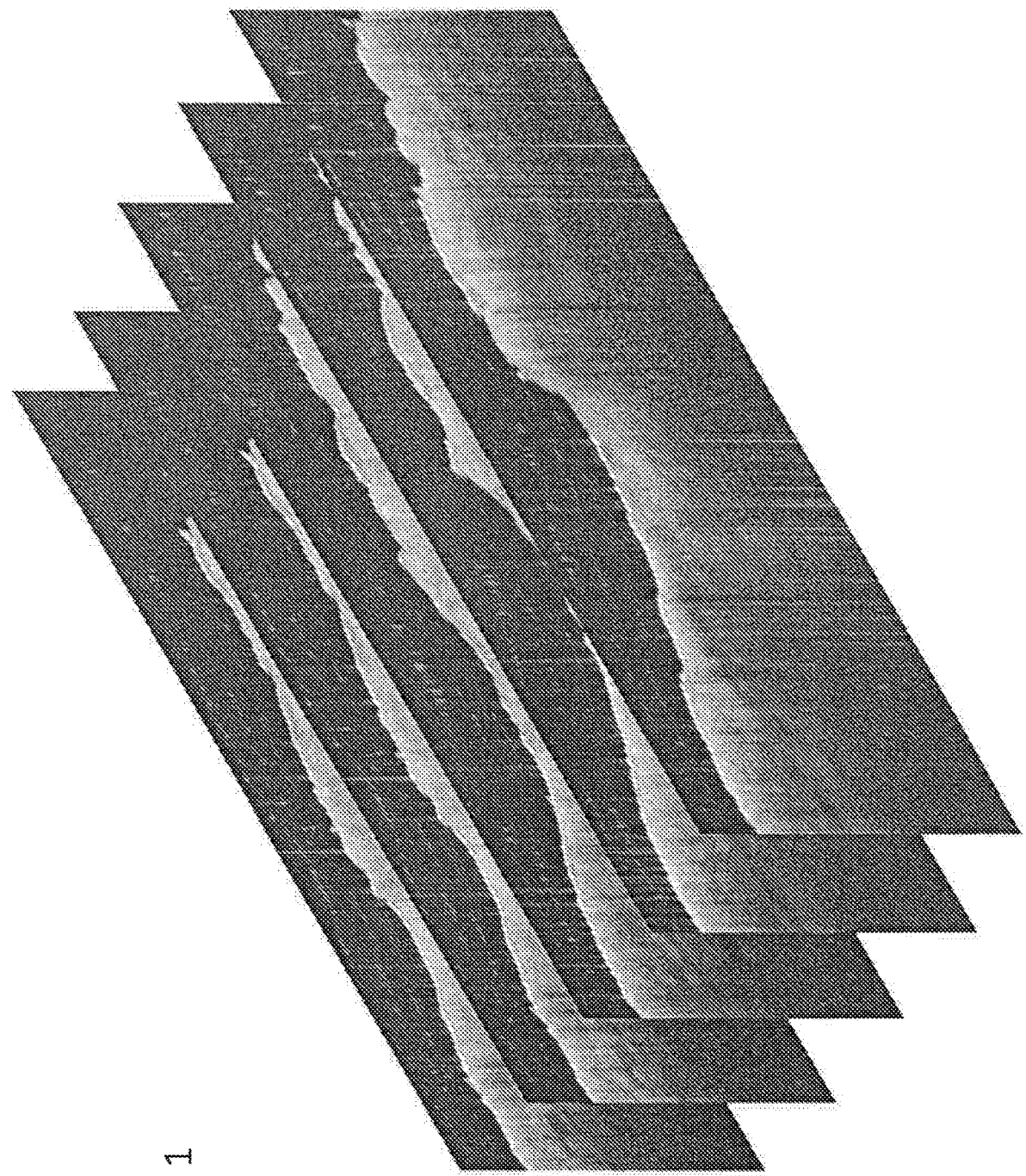
FIG. 1 shows a stack of OCT scans.

In recent years, Optical Coherence Tomography (OCT) has become widely used in the field of dermatology, especially as an aid to making diagnoses of skin cancer and other common skin conditions (Ulrich, M., T. Braunmuehl, H. Kurzen, T. Dirschka, C. Kellner, E. Sattler, C. Berking, J. Welzel, and U. Reinhold. "The sensitivity and specificity of optical coherence tomography for the assisted diagnosis of nonpigmented basal cell carcinoma: an observational study." British Journal of Dermatology 173, no. 2 (2015): 428-435.). OCT may be used to capture images of the sub-surface structure of the skin that reveal many potentially useful skin parameters that might be useful for controlling laser parameters. The following publications describe some such measurements:

Avanaki, M. R. and Hojjatoleslami, A., 2013. Skin layer detection of optical coherence tomography images. *Optik-International Journal for Light and Electron Optics*, 124(22), pp. 5665-5668.

Maiti, R., Gerhardt, L. C., Lee, Z. S., Byers, R. A., Woods, D., Herrera, J. A. S., Franklin, S. E., Lewis, R., Matcher, S. J. and Cane, M. J., 2016. In vivo measurement of skin surface strain and sub-surface layer deformation induced by natural tissue stretching. Journal of the Mechanical Behavior of Biomedical Materials.

Lu, Z., Boadi, J., Danby, S., Cork, M. and Matcher, S. J., 2013, March. Optical coherence tomography demonstrates differential epidermal thinning of human forearm volar skin after 2 weeks application of a topical corticosteroid vs a non-steroidal anti-inflammatory alternative. In SPIE BiOS (pp. 85650C-85650C). International Society for Optics and Photonics.

Babalola, O., Mamalis, A., Lev-Tov, H. and Jagdeo, J., 2014. Optical coherence tomography (OCT) of collagen in normal skin and skin fibrosis. Archives of dermatological research, 306(1), pp. 1-9.

Themstrup L, Welzel J, Ciardo S, Kaestle R, Ulrich M, Holmes J, Whitehead R, Sattler E C, Kindermann N, Pellacani G, Jemec G B. Validation of Dynamic optical coherence tomography for non-invasive, in vivo microcirculation imaging of the skin. Microvascular research. 2016 May 25.

Example skin parameters include (but not necessarily limited to):
1. Skin roughness
2. Depth of wrinkles
3. Skin reflectivity
4. Depth of epidermis
5. Depth of superficial vascular plexus in the upper dermis
6. Density of vessels in the superficial vascular plexus in the upper dermis
7. Average and upper and lower quartile diameters of superficial vascular plexus in the upper dermis
8. Optical attenuation versus depth
9. Colour (degree of pigmentation with melanin)
10. Epidermal thickness
11. Density of skin appendages (hairs and pores per unit area)

Each of these parameters can be measured in an OCT device.

Figure 9:
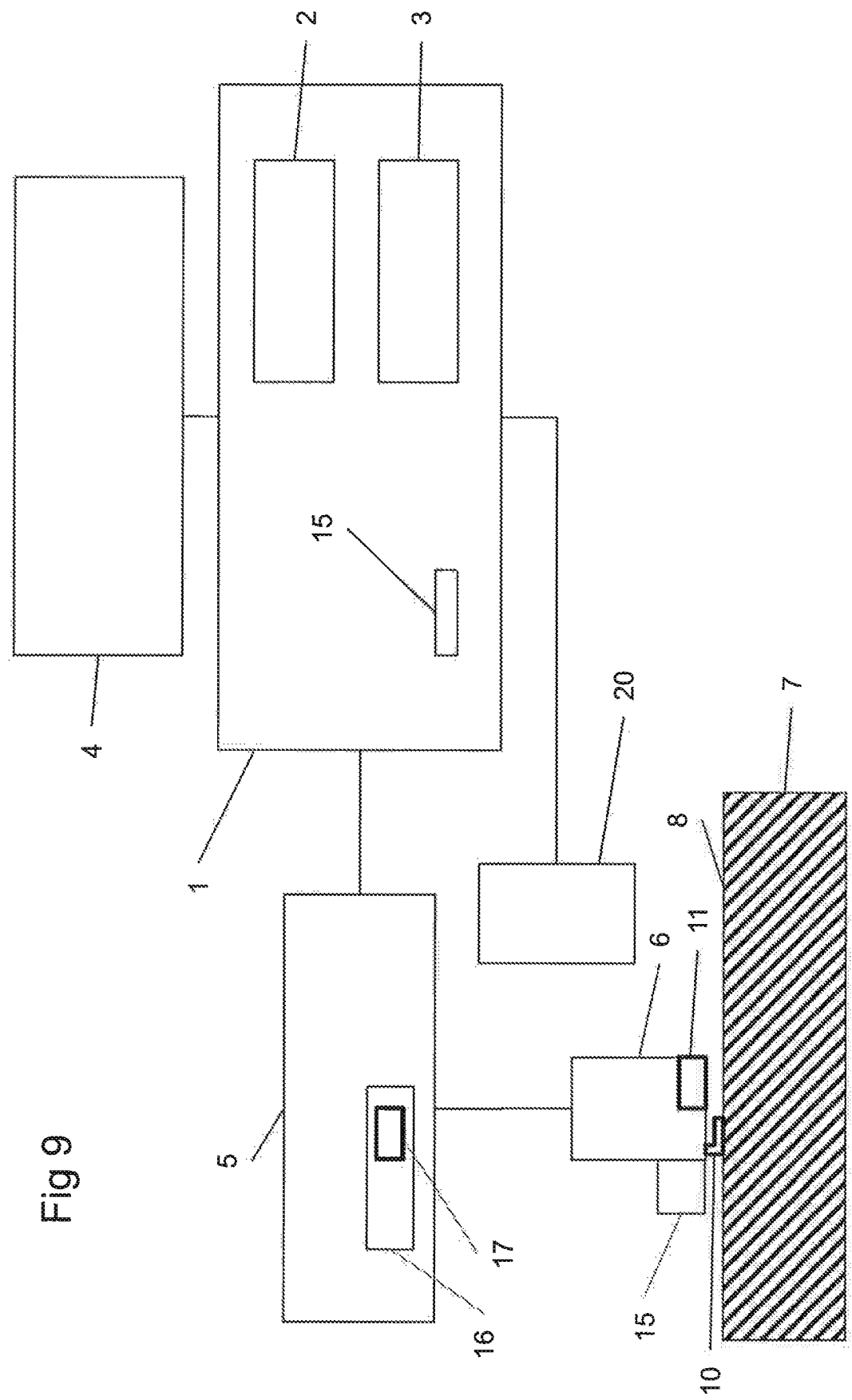
FIG. 9 shows schematically an optical coherence tomography (OCT) apparatus in accordance with an embodiment of the invention.

An optical coherence tomography (OCT) apparatus in accordance with an embodiment of the invention is shown in FIG. 9 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft (RTM) Windows (RTM) or Apple (RTM) Mac OS X (RTM) can be used. The computer 1 is also provided with a display 4 controlled by the processor 2 on which any desired graphics can be displayed, and a sound output device 15 such as a buzzer which can sound an alert noise.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight (RTM) apparatus available from Michelson Diagnostics of Orpington, Kent, United Kingdom. A stand-off 10 can be provided which spaces the probe 6 from the subject's skin 7.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin. By taking multiple scans spaced apart perpendicularly to the scans—and so parallel to the skin—a stack of scans can be formed, covering a volume of the subject's skin.

Figure 2:
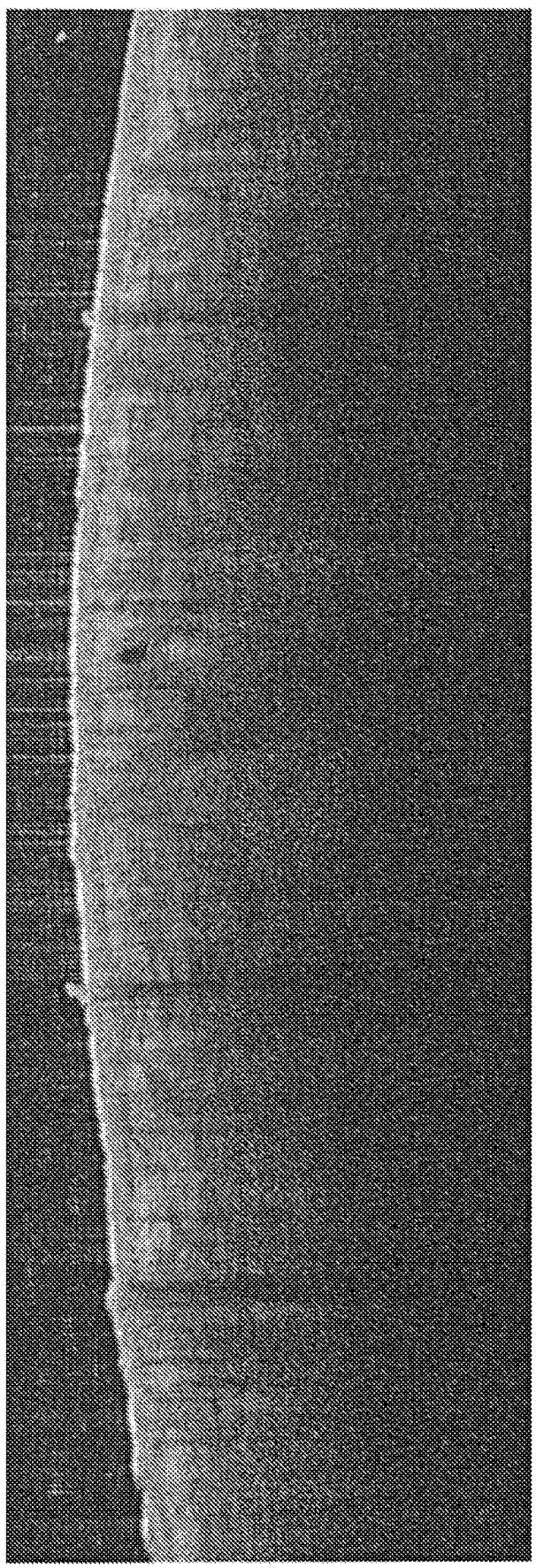
FIG. 2 shows a single OCT scan taken from the stack of FIG. 1.
Figure 3:
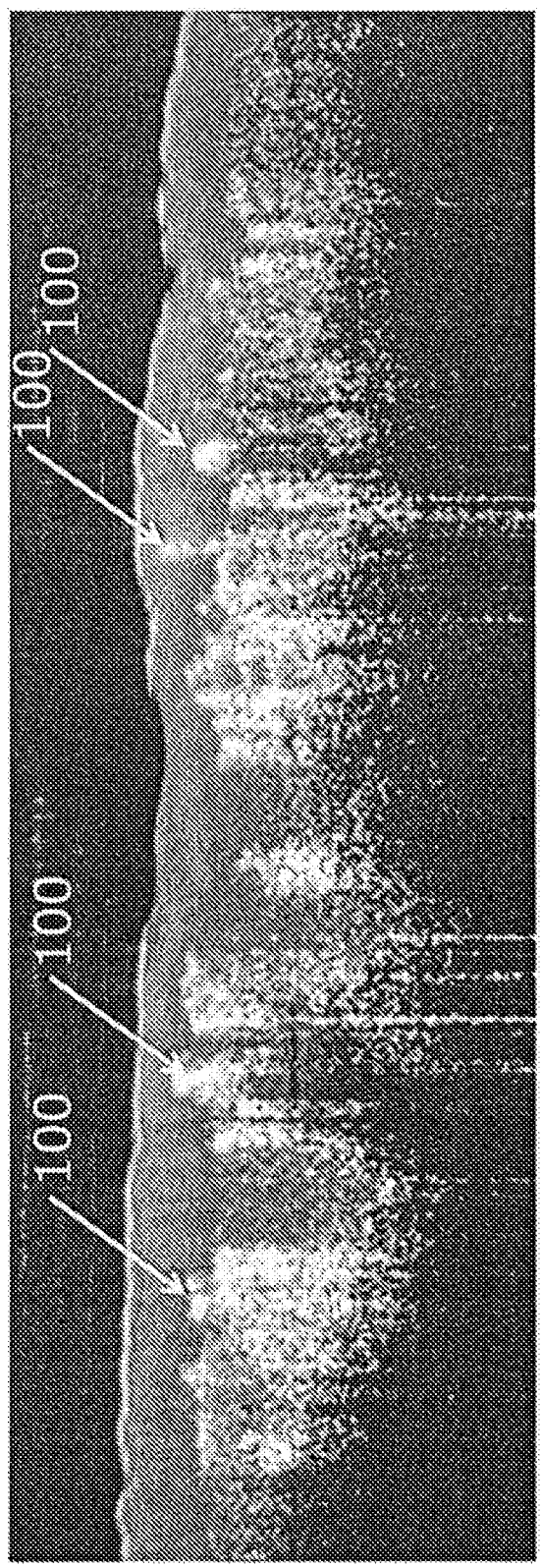
FIG. 3 shows blood vessels within a sample OCT scan.
Figure 4:
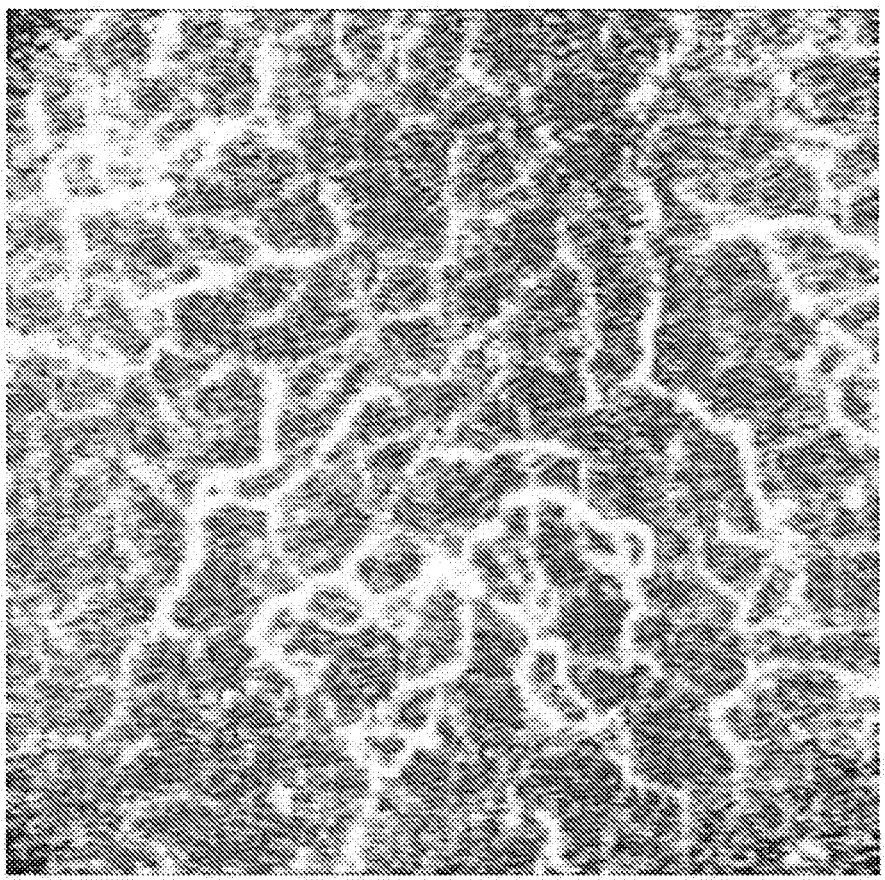
FIG. 4 shows a segmented en face OCT image showing blood vessels.

In one scan procedure, this device captures, a set of typically 120 (or more) OCT sub-images over a region of skin measuring 6 mm×6 mm. Each individual OCT sub-image comprises a depth-resolved OCT image of tissue 6 mm in width and 2 mm deep. This is shown diagrammatically in FIG. 1 of the accompanying drawings and an example sub-image is shown in FIG. 2 of the accompanying drawings. Furthermore, each OCT sub-image comprises OCT data collected from the same location but at slightly different times. These OCT sub-images collected at slightly different times are then processed using statistical algorithms that are well known by those skilled in the art, to detect regions of the skin that are in motion and are not static, these regions generally being found to be in motion due to the presence of blood flowing in superficial blood vessels. Therefore, the presence and morphology of blood vessels can be seen in the OCT sub images, as shown in FIG. 3 of the accompanying drawings, where blood vessels have been highlighted with arrows 100. The 120 sub images can be resampled at a constant depth to produce top-down instead of side-view images, known as 'en-face' images, and these can reveal the blood vessel network below the skin surface as shown in FIG. 4 of the accompanying drawings. The complete 'stack' of OCT sub-images collected during the scan procedure comprises a set of data that can then be further analysed to extract parameters of interest relevant to the success of the laser treatment.

Figure 5:
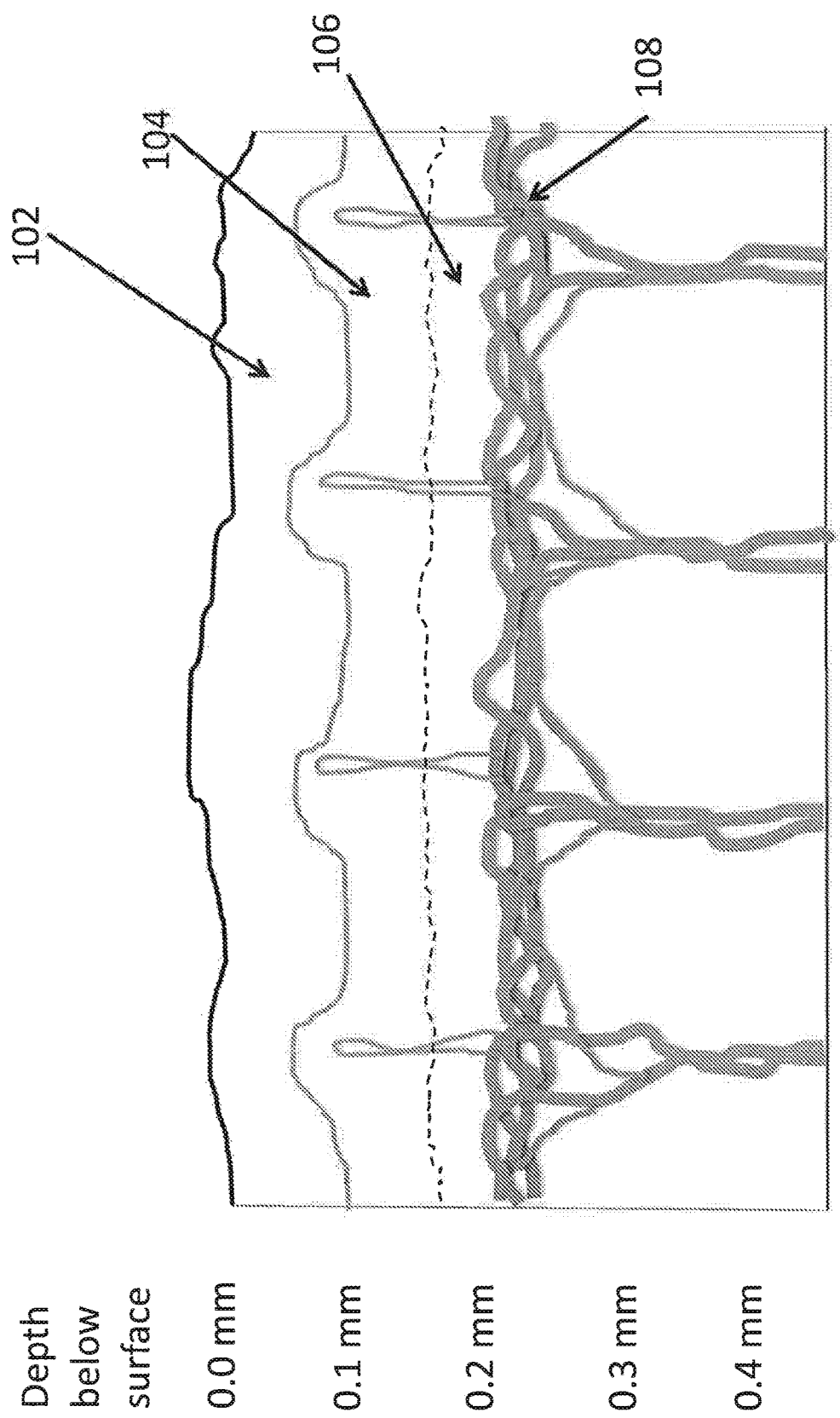
FIG. 5 shows schematically the structure of human skin.

As noted above, the capability of tissue that has been ablated or otherwise damaged by laser treatment to heal, depends upon the nature of the tissue and especially the depth of the treatment in relation to the thickness of the skin layers and structures. The structure of the upper skin layers is shown diagrammatically in FIG. 5 of the accompanying drawings. FIG. 5 shows the epidermis 102, the papillary dermis 104, the upper reticular dermis 106 and the superficial plexus 108. It is known that if only the epidermis 102 is damaged or removed, then the skin rejuvenation results are very unsatisfactory. It is believed by those skilled in the art that removal of the papillary dermis 104 produces acceptable results. It is known that removal of deeper layers of the dermis can cause scarring. The upper reticular dermis 106, which is located immediately below the papillary dermis 104 at a depth of 0.2 mm-0.5 mm, contains the superficial plexus 108, which is a dense 'mesh' or network of blood vessels. Removal of or serious damage to this superficial plexus seriously limits the capability of the skin to heal quickly without scarring. Thus, we have appreciated that the depth of the superficial plexus 108 is a key parameter for successful rejuvenation laser treatment.

Figure 6:
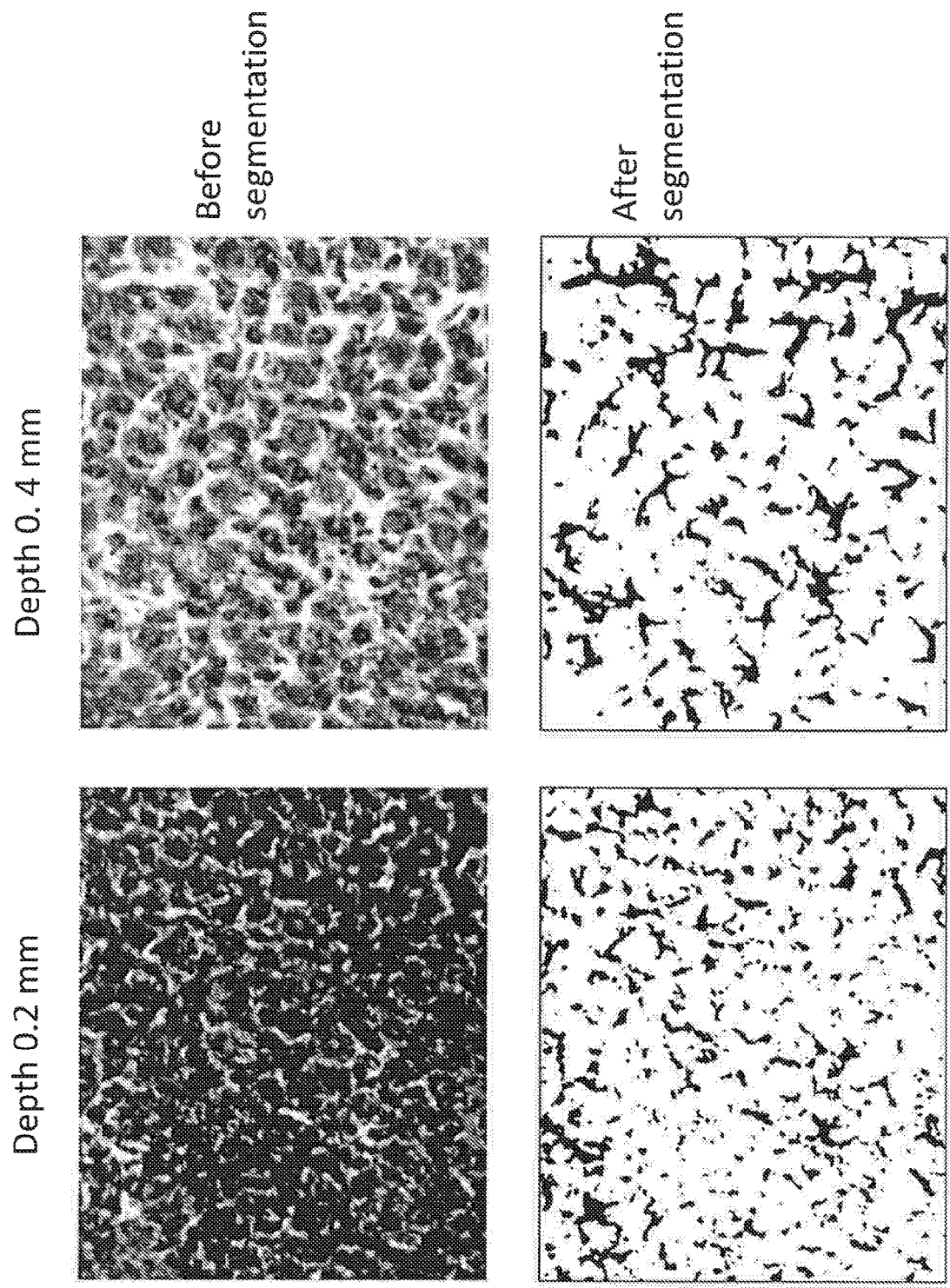
FIG. 6 shows en face images of a subject's skin at different depths before and after segmenting.

The data collected by the above-described OCT device can be processed to extract the depth of the superficial plexus. First, the top surface of the skin is detected across the whole data set, using an algorithm as described in the PCT patent application publication WO 2015/001317. Second, the blood vessel network is detected as described in PCT patent application publication WO 2016/135454 or via another method such as in Mariampillai, A., Standish, B. A., Moriyama, E. H., Khurana, M., Munce, N. R., Leung, M. K., Jiang, J., Cable, A., Wilson, B. C., Vitkin, I. A. and Yang, V. X., 2008. Speckle variance detection of microvasculature using swept-source optical coherence tomography. Optics letters, 33(13), pp. 1530-153, or: Wang, R. K., An, L., Saunders, S. and Wilson, D. J., 2010. Optical microangiography provides depth-resolved images of directional ocular blood perfusion in posterior eye segment. Journal of biomedical optics, 15(2), pp. 020502-020502. Third, the depth at which the superficial plexus is located is detected, by performing a segmentation operation on the blood vessel data at each depth and finding the depth at which there is more than a predetermined number of vessel segments with a length greater than a predetermined threshold. Example images are shown in FIG. 6 of the accompanying drawings before and after segmentation showing the variation in numbers of length segments.

Figure 7B:
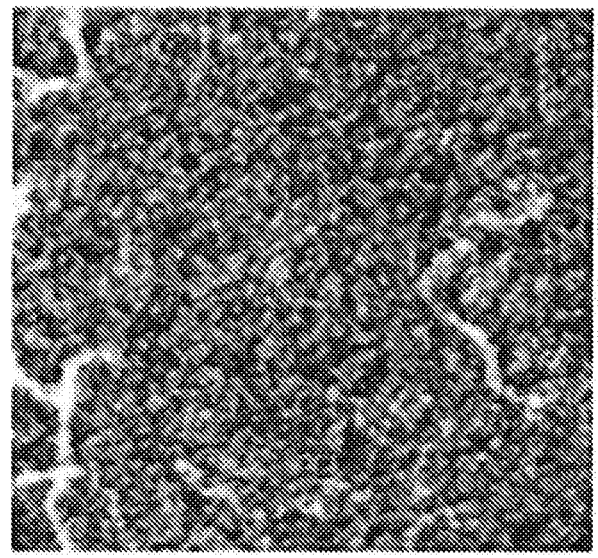
FIGS. 7a and 7b shows en face images of a subject's skin in the cheek and neck.
Figure 7A:
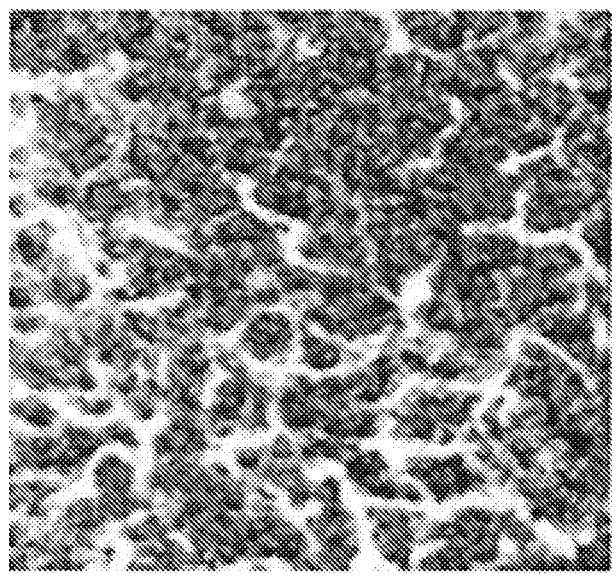

Another parameter that is of interest is the density of the vessels in the superficial plexus. Low density of vessels may correspond to poor healing potential, requiring a less aggressive laser treatment setting. FIGS. 7a and 7b of the accompanying drawings show examples of OCT images of vessel networks in the cheek (FIG. 7a) and the neck (FIG. 7b). It is known that neck skin has much poorer healing response than cheek skin. The OCT data can be processed to determine the density of vessels in the superficial plexus, by counting the number of vessel segments per unit area.

Also of interest is the vessel diameter. Unhealthy skin may have thinner vessels than healthy skin. The OCT data can be further processed to determine the average, median, upper and lower quartile diameters of vessels in the superficial plexus by extracting the dimensions of each vessel segment.

Figure 8B:
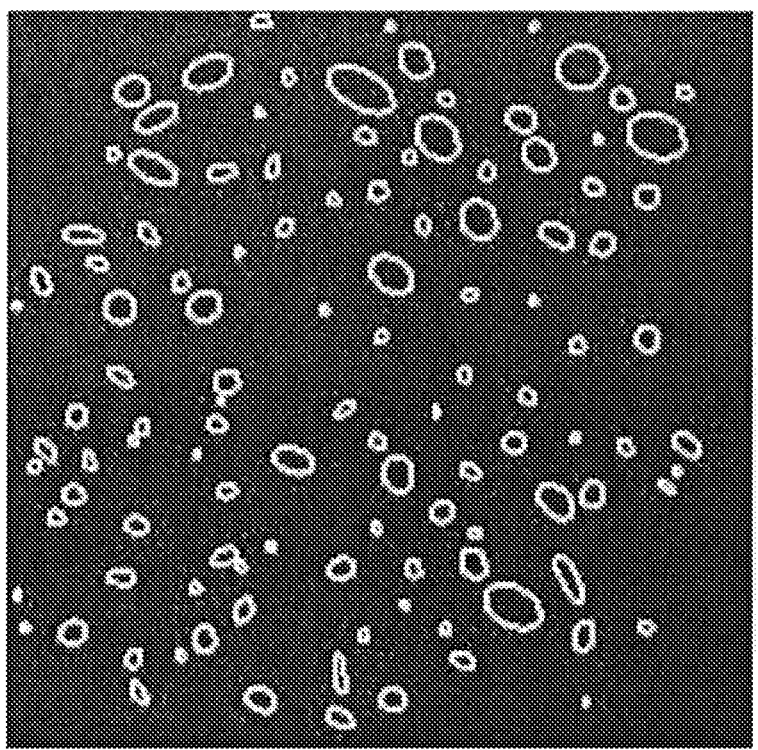
FIG. 8 shows images of a subject's skin before and after segmentation.
Figure 8A:
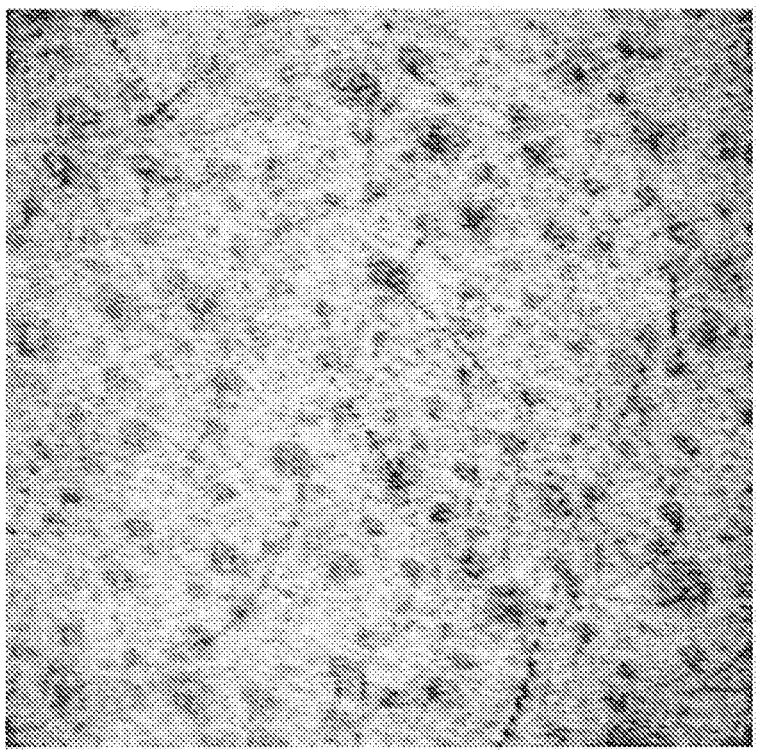

There may be further parameters extracted from the OCT image that can be additionally used to refine the estimate of maximum safe laser treatment depth obtained from the above process. These may include:

The density of skin appendages (hairs and pores), which can be obtained by segmenting the structural (non-dynamic) en-face OCT images at a depth just below the epidermis/dermis junction and calculating the number-density of features (as shown in FIGS. 8a and 8b of the accompanying drawings; FIG. 8a shows an en face OCT image, whereas FIG. 8b shows the corresponding image segmented to show pores and hair follicles)

The optical attenuation of the skin, which is the rate at which the OCT signal falls with depth below the skin surface. This has been found to be higher for skin that has a high density of collagen.

Skin roughness, which is a measure of the surface topography of the skin. The determination of the skin roughness may comprise the determination of the mean deviation of the skin position from the mean skin position (known as $R_a$), the range of skin position from the highest peak to lowest valley (known as $R_z$) or the root mean square deviation of the skin position (known as $R_q$). More wrinkled skin has higher $R_a$, $R_q$ and $R_z$ and may require more aggressive treatment to achieve an acceptable result.

Skin colour. The OCT device such as the VivoSight (RTM) may have an integrated colour camera that can capture images of the tissue being scanned; skin that has a higher melanin content will appear darker and this may result in different depth of penetration of the laser treatment than light coloured skin with low melanin.

This embodiment will provide a means for generating a set of control settings for the energy-delivery device 20, which is arranged to deliver energy to the skin 7. Typically, the settings will depend on the details of the energy-delivery device, such as the type of energy (visible/IR/UV light, RF etc.), wavelength, optical delivery system, and the exact manufacturer specifications of the control system for the device. The settings will also depend upon the operator's desired effect on the tissue, and on which settings are adjustable, such as the pulse duration, and fluence (energy delivered per unit area).

Typically, we would envisage that studies have been performed in which OCT scans were carried out on a number of subjects who were then treated with an energy-delivery device, and then analysis of the data carried out to establish which skin parameters are relevant to the treatment, and how they are correlated with the treatment settings resulting in optimal, and suboptimal effects on the tissue. Thus, the correlation enables a given set of OCT tissue measurements to be translated into a set of optimal control settings for the energy-delivery device.

In one embodiment, this correlation is embodied in the form of a look-up table, the table entries comprising the total possible (and observed) set of OCT measurements of the skin, and the associated optimal control settings for the energy-delivery device.

In an alternative embodiment, the correlation is embodied in the form of a computer algorithm which has parameters derived by studying the study data and/or calculations of the physics of the energy based treatment.

The derived control settings can then be further modified by utilising an input manually or automatically entered by the operator; such input being a means to further refine the treatment under the user's control to achieve a desired end result. For example, the user input may be a control 0-100% of the maximum safe optimal settings obtained by the look-up table or computer algorithm. Thus, the user may decide to apply 50% of the maximum optimal dose for reasons specific to the patient or treatment regime.

The resulting control settings can be transmitted to the energy-delivery device so that the operator can then use the energy based device to treat the tissue on the patient. The transmission may be by radio (e.g. by Wireless or Bluetooth) or by cable (e.g. by local intranet).

Whilst in this embodiment, the computing device for obtaining the control settings is that of the OCT apparatus, the processing may be carried out on one or more independent processing devices. The processing device(s) may be located on the OCT device from which the scans were obtained, with the settings transmitted to the energy-delivery device.

Alternatively, at least one of the processing devices can be located on the energy-delivery device instead. In this aspect, the OCT scans are transmitted to the energy-delivery device, and the processing to arrive at the control settings is done locally on the energy based device.

In a yet further embodiment, at least one processing device is located elsewhere than the OCT apparatus or the energy-delivery device, such as a server located in the vicinity or remotely—"in the cloud". In this embodiment, the OCT scans are transmitted to the server which then returns the optimal control settings, either to the OCT device for subsequent transmission to the energy-delivery device, or directly to the energy based device.

This has several advantages:
- The algorithm or look-up table can be updated by a third party, for example the manufacturer of the OCT device or the energy-delivery device, to improve or correct the settings that are used, in response to new experimental data, or updates to either the OCT or energy based equipment
- Every use of the invention can be remotely monitored by a third party, for example the manufacturer of the OCT device or the energy-based device, for aid in billing the operator for the use of the invention.

In another embodiment, the OCT scanner and the energy-delivery device, and one or more processing device, are all built into one single physical device, which may thereby perform all of the required calculations entirely by itself, or alternatively may access a remote server.

Generally, the transmission of the data to the energy-delivery device is kept secure, by means of data encryption, so that the transmitted settings may not be used to control the settings of another manufacturer's energy-based device.

In an embodiment, several OCT devices could be connected to multiple types of energy-delivery devices, with each type of energy-delivery device having its own method (look up table or algorithm) for obtaining the optimal control settings relevant to that specific device. Thus one OCT device could thereby 'service' multiple energy-delivery devices in a single user-setting.

The settings transmitted to the control unit of an energy-delivery device can be coded with the physical location of the OCT scan on the subject, and can be transmitted at a later time. This is entered manually by the operator, or captured automatically in a pre-set sequence of scans, each triggered by the operator pressing a button on the probe, or by voice control, or other means. This aspect enables the operator to perform a sequence of OCT scans on multiple locations, for example on different parts of the patient's face, in one session, and then to perform all of the energy-based treatments of these specific locations at second session on the same day or at a later date. This aspect has the advantage of maximising the efficient use of both the OCT device and the energy-delivery device.

The invention claimed is:

1. A method of processing optical coherence tomography (OCT) scans through a subject's skin, the method comprising, using a computing device:
    receiving a plurality of OCT scans through the subject's skin, the OCT scans representing an OCT signal in slices through the subject's skin;
    processing the OCT scans to determine a set of parameters, including determining a depth of the superficial plexus through the subject's skin as one of the parameters, wherein determining a depth of the superficial plexus comprises at least one:
    a) performing a segmentation operation on blood vessel data at each depth and finding the depth at which there is more than a predetermined number of vessel segments with a length greater than a predetermined threshold;
    b) determining a density of blood vessels at each depth and finding the depth at which the blood vessel density exceeds a predetermined threshold;
    processing each parameter to determine a set of control settings for an energy-delivery device;
    transmitting the control settings from the computing device to the energy-delivery device;
    wherein the superficial plexus is found between 0.2 and 0.5 mm below a surface of the subject's skin.

2. The method of claim 1, in which the control settings comprise a range of depths to which energy is to be delivered, with a maximum depth being less than, or proportional to, the depth of the superficial plexus.

3. The method of claim 1, in which the depth of the superficial plexus is determined by determining a profile of lengths of blood vessel segments in the scans at varying depth.

4. The method of claim 3, in which the depth of the superficial plexus is determined by the method of step a).

5. The method of claim 1, in which the determination of the depth of the superficial plexus comprises determining a position of a surface of the subject's skin in the scans.

6. The method of claim 1, in which the set of parameters comprises at least one of:
    a) a density of vessels in the superficial plexus; and
    b) blood vessel diameter, particularly of the superficial plexus.

7. The method of claim 1, in which the set of parameters comprises an indication of a level of skin appendages in the subject's skin.

8. The method of claim 7, in which skin appendages comprise at least one of hairs and follicles.

9. The method of claim 7, in which the determination of the level of skin appendages comprises building an en-face scan of the subject's skin, and determining a presence of skin appendages therein.

10. The method of claim 9, in which the en-face scan is built at a depth through the skin below but adjacent to the epidermis-dermis junction.

11. The method of claim 1, in which the set of parameters comprises at least one of:
    an optical attenuation of the skin
    skin roughness
    skin colour Depth of wrinkles
Skin reflectivity
Depth of epidermis
Density of vessels in the superficial vascular plexus in the upper dermis
Optical attenuation versus depth.

12. The method of claim 1, in which the energy delivery device comprises at least one of:
a laser
Full-field ablative laser
Fractional ablative laser
Non-ablative laser
Intense Pulse Light.

13. The method of claim 1, in which the control settings comprise at least one of:
pulse duration
pulse energy
fluence (that is, energy delivered per unit area)
beam depth
beam diameter
number of pulses per treatment.

14. The method of claim 1, comprising allowing an operator to modify the control settings before they are used in the energy-delivery device.

15. The method of claim 1, comprising using the control settings in the energy-delivery device to deliver energy to the subject's skin.

16. The method of claim 1, in which the plurality of scans are captured using an OCT apparatus, and in which the processing of the skin parameters from OCT scans to obtain control settings is performed on the OCT apparatus.

17. The method of claim 1, in which the processing of the skin parameters from OCT scans to obtain control settings is performed on the energy delivery device.

18. The method of claim 1, in which the processing of the skin parameters from OCT scans to obtain control settings is performed at a remote location by a remote processing means, typically connected to the energy delivery device via the internet.

19. Apparatus for processing optical coherence tomography (OCT) scans through a subject's skin, the apparatus comprising a computing device arranged to:
receive a plurality of OCT scans through the subject's skin, the OCT scans representing an OCT signal in slices through the subject's skin;
process the OCT scans to determine a set of parameters, including determining a depth of the superficial plexus through the subject's skin as one of the parameters, wherein determining a depth of the superficial plexus comprises at least one:
a) performing a segmentation operation on blood vessel data at each depth and finding the depth at which there is more than a predetermined number of vessel segments with a length greater than a predetermined threshold;
b) determining a density of blood vessels at each depth and finding the depth at which the blood vessel density exceeds a predetermined threshold;
process each parameter to determine a set of control settings for an energy-delivery device;
transmit the control settings to the energy-delivery device;
in which the set of parameters comprises a depth of the superficial plexus through the subject's skin, wherein the superficial plexus is found between 0.2 and 0.5 mm below a surface of the subject's skin.

20. The apparatus of claim 19, comprising a camera arranged to capture an image of the skin.

21. A skin energy-delivery apparatus comprising the apparatus of claim 19, and an energy-delivery device arranged to deliver energy to a subject's skin.

* * * * *